United States Patent [19]

Forster et al.

[11] 4,450,308

[45] May 22, 1984

[54] PROCESS FOR THE PREPARATION OF TRIFLUOROMETHYLPHENYL OXYPHENYL ETHER COMPOUNDS

[75] Inventors: Heinz Forster, Wuppertal; Uwe Priesnitz, Solingen, both of Fed. Rep. of Germany

[73] Assignee: Bayer Aktiengesellschaft, Leverkusen, Fed. Rep. of Germany

[21] Appl. No.: 325,809

[22] Filed: Nov. 30, 1981

Related U.S. Application Data

[63] Continuation of Ser. No. 226,348, Jan. 19, 1981.

[30] Foreign Application Priority Data

Feb. 8, 1980 [DE] Fed. Rep. of Germany ....... 3004695

[51] Int. Cl.³ ............................................. C07C 41/16
[52] U.S. Cl. ................................................... 568/637
[58] Field of Search ......................................... 568/637

[56] References Cited

U.S. PATENT DOCUMENTS

3,966,453 6/1976 Takahashi et al. ............. 568/639 X
3,966,826 6/1976 Trosken ............................. 568/637

FOREIGN PATENT DOCUMENTS

351 6/1978 European Pat. Off. .
359 6/1978 European Pat. Off. .
3562 2/1979 European Pat. Off. .
2333848 1/1975 Fed. Rep. of Germany .

*Primary Examiner*—Bernard Helfin
*Attorney, Agent, or Firm*—Felfe & Lynch

[57] ABSTRACT

New process for the preparation of known trifluoromethylphenyl oxyphenyl ether compounds of the formula

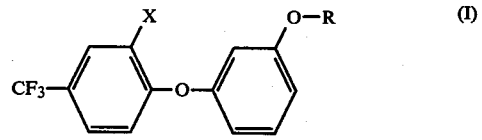

wherein
X stands for fluorine, chlorine or bromine and
R for moieties, substituted if desired, of the series alkyl, alkenyl and alkinyl, by reacting 1,2-dihalogen-4-trifluoromethylbenzenes of the formula

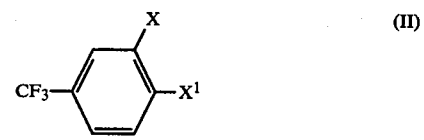

in which X and $X^1$ independently of one another stand for fluorine, chlorine or bromine, with phenols of the formula

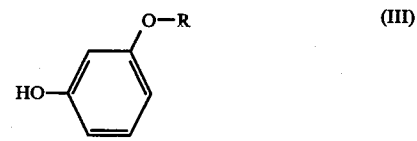

in which R has the meaning given above, and basic alkali or alkaline earth compounds or with the salts formed from the phenols of formula (III) and the basic alkali or alkaline earth compounds, in the presence of diluents at temperatures between 60° and 120° C.

The compounds of the formula (I) are intermediates for the synthesis of herbicides.

2 Claims, No Drawings

PROCESS FOR THE PREPARATION OF TRIFLUOROMETHYLPHENYL OXYPHENYL ETHER COMPOUNDS

This is a continuation of application Ser. No. 226,348, filed Jan. 19, 1981 and now abandoned.

The invention relates to a new process for the preparation of known trifluoromethylphenyl oxyphenyl ether compounds. Such compounds are intermediates for the synthesis of herbicides.

It is already known that certain trifluoromethylphenyl phenyl ethers, such as for example (2-chloro-4-trifluoromethyl-phenyl)-(3-methoxy-phenyl) ether are obtained if 4-trifluoromethyl-1-halogen-benzenes are heated for a relatively long time at approximately 140° C. with alkali phenolates, such as for example sodium-3-methoxyphenolate, in polar solvents such as dimethylsulfoxide, for example (cf. DE-OS No. 2,333,848). By this process, however, greatly contaminated products are obtained in unsatisfactory yields. The solvent dimethylsulfoxide, which is mostly used in this process, also decomposes exothermically at temperatures above 130° C.; therefore, the known process is poorly suited for performance on the large technical scale.

Now, it has been found that trifluoromethylphenyl oxyphenyl ethers of the formula

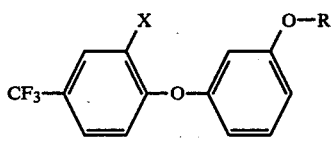

wherein
X stands for fluorine, chlorine or bromine and
R for moieties, substituted if desired, of the series alkyl, alkenyl and alkinyl,
are obtained when 1,2-dihalogen-4-trifluoromethylbenzenes of the formula

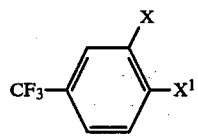

in which X and $X^1$ independently of one another stand for fluorine, chlorine or bromine,
are reacted with phenols of the formula

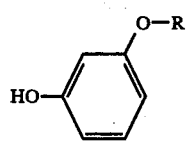

in which R has the meaning given above, and basic alkali or alkaline earth compounds or with the salts formed from the phenols of Formula (III) and the basic alkali or alkaline earth compounds, in the presence of diluents at temperatures between 60° and 120° C.

It is to be considered as surprising that, by the process of the invention, trifluoromethylphenyl oxyphenyl ethers of Formula (I) are obtained in very good yields and in high purity at reaction temperatures greatly reduced in comparison to the state of the art, without any lengthening of the otherwise common reaction time.

The process of the invention has a number of advantages. For example, unnecessary energy consumption is avoided by performance at relatively low temperature; the endangerment of the environment is reduced; the formation of undesired by-products is greatly limited, and the yield of the compounds of Formula (I) is increased accordingly.

The process of the invention thus represents a valuable enrichment of the art.

If, for example, 1,2-dichloro-4-trifluoromethylbenzene and potassium-3-methoxyphenolate are used as starting substances, the reaction can be given by the following formula:

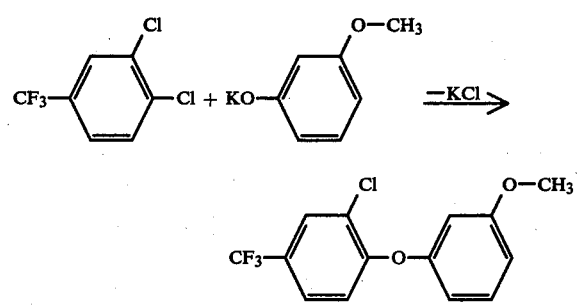

The 1,2-dihalogen-4-trifluoromethylbenzenes to be used as starting substances are generally defined by Formula (II). In this Formula (II), X and $X^1$ stand preferably for chlorine. Preferred starting compound of Formula (II) is thus 1,2-dichlor-4-trifluoromethylbenzene.

Compounds of Formula (II) are already known (cf. U.S. Pat. No. 3,928,416).

The phenols also required as starting substances are defined by Formula (III). Preferably, R therein represents alkyl with up to 4 carbon atoms, especially methyl.

Especially preferred starting compound of Formula (III) is thus 3-methoxyphenol.

Starting compounds of Formula (III) are also previously known.

Virtually all inert organic solvents can serve as the diluent. These include especially aliphatic and aromatic hydrocarbons, which may be halogenated if desired, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as acetic acid methyl ester and ethyl ester, nitriles such as acetonitrile and propionitrile, amides such as dimethylformamide, dimethylacetamide and N-methylpyrrolidone, as well as dimethylsulfoxide, tetramethylenesulfone and hexamethyl phosphoric acid triamide.

Of the diluents named, the aprotic polar solvents are used preferentially, especially dimethylsulfoxide and additionally, if desired, other solvents such as toluene or xylenes.

Basic alkali or alkaline earth compounds which can be used in the process of the invention are, for example, alkali or alkaline earth oxides, hydroxides, carbonates, hydrides, amides and alcoholates.

Examples of compounds of this series are sodium and potassium hydroxide, calcium oxide and hydroxide, potassium carbonate, sodium and calcium hydride, sodium amide, as well as sodium ethylate and potassium tert.-butylate.

Sodium and potassium hydroxide are used preferentially.

The reaction temperature in the performance of the process of the invention is maintained between 60° and 120° C., preferably between 80° and 110° C. In general it is performed at standard pressure. It is also possible, however, to perform the process at slightly elevated or reduced pressure, say between 0.1 and 10 bars.

1 to 1.5 moles, preferably 1.1 to 1.4 moles, of phenol of Formula (III) and 1 to 2 moles, preferably 1.1 to 1.5 moles, of a basic alkali compound or a corresponding molar equivalent of a basic alkaline earth compound are used to 1 mole of 1,2-dihalogen-4-trifluoromethylbenzene of Formula (II).

In general, the process of the invention is performed by first placing a phenol of Formula (III) together with a basic alkali or alkaline earth compound in a solvent, removing azeotropically any water that forms, then adding a 1,2-dihalogen-4-trifluoromethylbenzene of Formula (II) in substance or in solution at room temperature, and then slowly heating the reaction mixture to the desired reaction temperature. It is also possible, however, to dissolve or disperse all of the reactants in the solvent at room temperature, that is, between 10° C. and 30° C., and then bring the complete mixture to the reaction temperature.

The working up is performed by conventional methods. In general the procedure is to concentrate the reaction mixture after the reaction has ended, add water and an organic solvent that is poorly soluble in water to the concentrate, and separate, wash, dry and concentrate the organic phase.

In a preferred embodiment of the process of the invention, first a phenol or Formula (III) is heated to ebullition with a basic alkali or alkaline earth compound, preferably in the presence of a diluent which forms an azeotropically boiling mixture with water, such as toluene for example, and the water formed in the reaction is continuously removed through a water separator. Then the reaction mixture is diluted with one of the above-given polar solvents and a 1,2-dihalogen-4-trifluoromethylbenzene of Formula (II) is added. The reaction mixture is stirred for a few hours, preferably 3 to 5 hours, at the above-given reaction temperature. For working up, the solvent is removed by vacuum distillation, the concentrate is stirred with water and an organic solvent that is immiscible with water, such as for example cyclohexane. Then the reaction mixture is suction filtered through silica gel. The organic phase is washed with dilute soda lye and then with water, dried and filtered. The solvent is carefully distilled out of the filtrate, the product remaining as an oily residue.

The trifluoromethylphenyl oxyphenyl ethers of Formula (I) which can be prepared by the process of the invention are valuable starting substances for the synthesis of substituted diphenyl ethers which have outstanding herbicidal properties (see German Published Specification De-OS No. 23 33 848).

For example, 2-chloro-4'-nitro-4-trifluoromethyl-4'-methoxydiphenyl ether of the formula

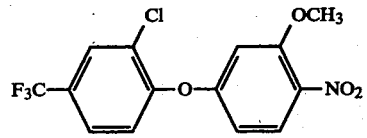

can be prepared by reacting (2-chloro-4-trifluoromethylphenyl)-(3-methoxy-phenyl) ether with nitric acid in the presence of glacial acetic acid and acetic anhydride. This synthesis can be represented formula-wise as follows:

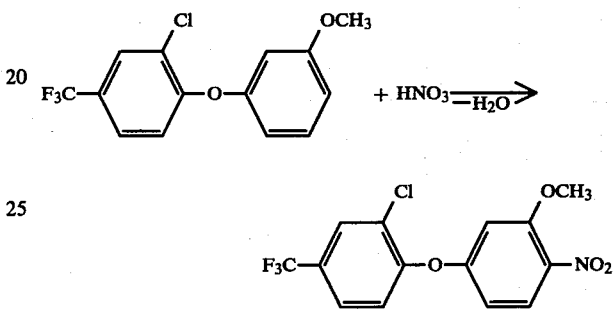

The process of the invention is represented by the following examples.

EXAMPLE 1

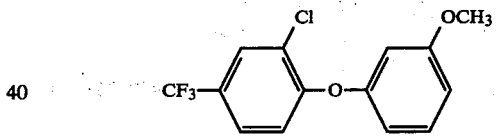

158 g (1.285 mol) of resorcinol monomethyl ether is heated, with refluxing, together with 500 ml of toluene and 82.4 g of potassium hydroxide powder. The water is continually removed azeotropically. 300 ml of dimethylformamide and 215 g (1.0 mol) of 1,2-dichloro-4-trifluoromethylbenzene are added to the remaining salt. The reaction mixture is slowly heated to 90° C. The reaction mixture is then held for 4 hours at 90°–100° C. The solvent is removed by vacuum distillation. Then 100 ml of water and 500 ml of cyclohexane are added and the mixture is thoroughly stirred. Then it is suction filtered through kieselgur and the cyclohexane phase is washed once with 1 N aqueous soda lye and then neutral with water. The solution is dried and concentrated in vacuo.

(2-chloro-4-trifluoromethyl-phenyl)-(3-methoxy-phenyl) ether is obtained as the concentrate in yields between 80 and 90% of the theory. Boiling point: 121°–125° C./1–2 mbar $^{22}n_D = 1.5331$.

Preparation of 2-Chloro-4'-nitro-4-trifluoromethyl-3'-methoxydiphenyl Ether Setting Out From (2-Chloro-4-trifluoromethyl-phenyl)-(3-methoxyphenyl) Ether

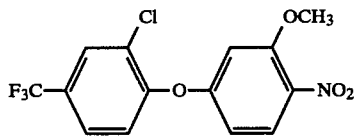

A solution of 8.35 ml (0.2 mol) of nitric acid (density 1.5) in 30 ml of acetic acid is added drop by drop to a solution of 60.5 g (0.2 mol) of (2-chloro-4-trifluoromethyl-phenyl)ether in 40 ml of acetic anhydride at 25° to 30° C. over a period of 30 minutes. The reaction mixture is stirred for 4 hours at 25° to 30° C. and then poured onto ice. It is extracted with methylene chloride, and the extraction solution is washed with water, with dilute soda lye, and again with water.

After withdrawal of the solvent the remaining product is purified by recrystallization from methanol.

36 g (51% of the theory) is obtained of 2-chloro-4'-nitro-4-trifluoromethyl-3'-methoxydiphenyl ether of a melting point of 103° C.

It will be understood that the specification and examples are illustrative but not limitative of the present invention and that other embodiments within the spirit and scope of the invention will suggest themselves to those skilled in the art.

What is claimed is:

1. Process for the preparation of (2-chloro-4-trifluoromethyl-phenyl)-(3-methoxy-phenyl)-ether of the formula

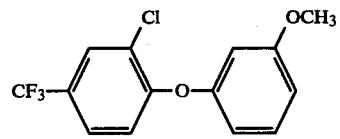

which process comprises reacting 1,2-di-chloro-4-trifluoromethylbenzene of the formula

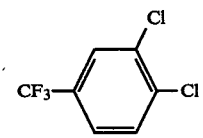

in the presence of a diluent, selected from the group consisting of dimethylformamide, dimethylsulfoxide, toluene or xylene and at a temperature of between 90° and 100° C. with resorcinol monomethyl ether of the formula

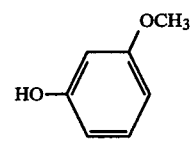

and potassium hydroxide, or with a salt formed from resorcinol monomethyl ether of the formula (III) and potassium hydroxide, the respective molar ratios of formula (II) to formula (III) to potassium hydroxide being 1:1–1.5:1–2.

2. Process as claimed in claim 1 wherein the reaction is carried out in dimethyl formamide as a diluent.

* * * * *